United States Patent

Wang et al.

[11] Patent Number: 5,876,349
[45] Date of Patent: Mar. 2, 1999

[54] METHOD AND APPARATUS FOR VENTRICULAR FIBRILLATION DETECTION

[75] Inventors: Jyh-Yun J. Wang, Newton; Michael Nakagawa, Cambridge, both of Mass.

[73] Assignee: Hewlett-Packard Company, Palo Alto, Calif.

[21] Appl. No.: 908,847

[22] Filed: Aug. 8, 1997

[51] Int. Cl.$^6$ ................................................. A61B 5/046
[52] U.S. Cl. ............................................................ 600/518
[58] Field of Search ............................... 607/5; 600/515, 600/517, 518

[56] References Cited

U.S. PATENT DOCUMENTS

| | | | |
|---|---|---|---|
| 4,181,135 | 1/1980 | Andressen et al. | 600/517 |
| 5,439,004 | 8/1995 | Duong-Van et al. | 600/518 |

OTHER PUBLICATIONS

S. Kuo and R. Dillman, "Computer Detection of Ventricular Fibrillation", Computers in Cardiology, pp. 347–349, Sep., 1978.

*Primary Examiner*—William E. Kamm
*Assistant Examiner*—George R. Evanisko

[57] ABSTRACT

Provided are a method and apparatus for assessing the chaotic nature of a waveform representation of heart function. The method and apparatus accomplish their objects via the following. An indicator of triangular-like components within a waveform representation of heart function is calculated. An indicator of an area encompassed by the waveform representation indicative of heart function is calculated. A ratio is calculated utilizing the calculated indicator of an area and calculated indicator of triangular-like components to assess the chaotic nature of the waveform representation of heart function. Additionally, a ventricular fibrillation index is calculated. The calculated ventricular fibrillation index is utilized, in two dimensional space, with the ratio that is calculated utilizing the calculated indicator of an area and the calculated indicator of triangular-like components to assess the likelihood of ventricular fibrillation based upon waveform representation of heart function. Further additionally, a minimum ventricular fibrillation index is calculated. The calculated minimum ventricular fibrillation index is utilized, in two dimensional space, with the ratio that is calculated utilizing the calculated indicator of an area and the calculated indicator of triangular-like components to assess the likelihood of ventricular fibrillation based upon waveform representation of heart function. The minimum calculated ventricular fibrillation is also utilized in one dimensional space to assess the likelihood of ventricular fibrillation based upon waveform representation of heart function.

30 Claims, 10 Drawing Sheets

Numerator = $\sum_j |V(j)|$ = Area

Denominator = $\sum_j |V(j) - V(j-1)|$ = 2H

METHOD AND APPARATUS FOR VENTRICULAR FIBRILLATION DETECTION

BACKGROUND

1. Technical Field

The present invention relates, in general, to a method and apparatus which yield an automated analysis of waveform representations of heart function. In particular, the present invention relates to a method and apparatus which yield an automated analysis of waveform representations of heart function produced by an electrocardiographic device.

2. Description of Related Art

The electrocardiogram (EKG) is a graphic recording of the electrical potentials generated by electrical activity in the heart. The electrical impulse formation and conduction associated with each cardiac contraction produce weak electrical currents that spread through the entire body. By applying electrodes to various positions on the body, and connecting these electrodes to an electrocardiographic apparatus, the variation in the magnitude of the electrical potential is recorded.

A normal EKG consists of a series of waves which are repeated with each cardiac cycle. These waves are labeled as P, QRS, and T according to convention. The P wave represents the depolarization and contraction of both atria, the QRS complex represents the depolarization and contraction of the ventricles, and the T wave represents the repolarization of the ventricles.

An arrhythmia (irregular heart beat) exists when the normal cardiac conduction is disturbed or interrupted. Arrhythmias can occur in many different forms, and have historically been grouped according to different characteristics of the arrhythmia. Arrhythmias can be grouped based on rate: bradyarrhythmias (rate too slow) and tachyarrhythmias (rate too fast). Arrhythmias can be grouped based on the originating site in the heart: atrial arrhythmias, junctional arrhythmias, and ventricular arrhythmias. And, arrhythmias can be grouped based on the underlying pathophysiologic mechanism of the arrhythmia: conduction abnormalities (caused by conduction block, reentry, or reflection), and impulse formation abnormalities (caused by altered automatic or triggered activity). While some arrhythmias are totally asymptomatic and benign (they do not affect the circulation, nor do they warn of the development of more serious arrhythmias), others can be symptomatic and life threatening (due to their impairment of the heart's ability to pump enough blood to meet the body's demands), eventually causing significant mortality and morbidity.

Ventricular fibrillation (VF) is a lethal arrhythmia. Its most frequent cause is coronary artery disease, and it is the most common terminal event in sudden cardiac death. VF occurs when multiple ectopic ventricular foci produce complete disruption of the normal order of ventricular excitation, resulting in a quivering motion of the ventricles. The surface EkG pattern is characterized by a rapid, repetitive series of chaotic waves without any identifiable QRS complexes. Due to the lack of coordinated electrical and mechanical activity, the heart becomes an ineffective pump and circulatory arrest occurs within seconds. The patient will die within minutes unless a normal spontaneous rhythm is restored, usually by electric defibrillation. Therefore, rapid and accurate recognition of VF is very important so that appropriate therapies can be initiated promptly.

Ventricular tachycardia (VT) is another arrhythmia which originated in the ventricles with a rate greater than 100 beats per minute by definition. There are several different forms of VT, including monomorphic (uniform QRS morphology), polymorphic (constantly changing QRS morphology), torsades de points (polymorphic VT with QT interval prolongation), and ventricular flutter (sinusoidal morphology). While nonsustained VT (VT with short duration and without hemodynamic collapse) is not immediately life threatening, VT with very rapid rate and/or long duration can cause serious hemodynamic deterioration and is always potentially life threatening. Clinical data has shown that most sudden cardiac death patients had VT as their initiating event that degenerated into ventricular fibrillation. Therefore, it is highly desirable to detect these immediate forerunners of VF episodes so that appropriate therapies can be initiated.

For this reason, several forms of VT, including high rate monomorphic VT, polymorphic VT (including torsades de points), and ventricular flutter are usually considered in the same life threatening category as ventricular fibrillation when designing automated detection methods for VF detection. Therefore, even though these detection methods are usually called VF detection method, they are in fact designed to detect both ventricular fibrillation and several forms of potentially life-threatening ventricular tachycardia as described above. From the detection method design viewpoint this is actually desirable, because due to the peculiar QRS morphologies associated with these VT waveforms, which are often -intermediary between VT and VF, it is very difficult to differentiate them from the true VF episodes.

A great amount of work has been done over the past twenty years to develop computer programs for automated VF detection. At present, the automated VF detection capability is an essential component in three major cardiac care devices, including (1) Real-time EKG/arrhythmia monitors, (2) Implantable cardioverter-defibrillators (ICDs), and (3) Automatic external defibrillators (AEDs). Clinical values of these devices in terms of life saving and morbidity reduction are well established despite the fact that the VF detection methods used in these devices are not perfect. Accuracy of these automated detection methods are measured in terms of false negative (true VF episode not detected) and false positive (non-VF episode detected as VF). For a given detection method design tradeoffs between false positive and false negative can usually be made by adjusting the detection threshold. While missed detection of a life-threatening tachyrhythmia episode may have significant impact on a patient's morbidity and mortality, false positive detection on the other hand has the potential of causing the patient to receive inappropriate treatments, which may also have undesirable consequences. Therefore, the ultimate goal of performance improvement is to reduce both the false negative and false positive, which cannot be achieved by just changing the detection threshold.

There are many different techniques which are currently utilized for automated VF/VT detection. One such technique has been described by S. Kuo and R. Dillman in *Computer Detection of Ventricular Fibrillation,* Computers in Cardiology, 1978, pp. 347–349, IEEE Computer Society, which is incorporated by reference herein in its entirety. The functioning of which will be briefly explained with reference to FIG. 3.

With reference to FIG. 3, the method can be briefly described as follows. First, the incoming EKG signal 300 is fed to AND Converter 302 which produces a sampled EKG signal $V_{(j)}$, which is then fed into Period Computation Unit 304. Period Computation Unit 304 calculates a period estimate T utilizing the following equation:

$$T = 2\pi \frac{\Sigma |V(j)|}{\Sigma |V(j) - V(j-1)|} \quad \text{(Eq. 1)}$$

Second, using the estimated period derived from Equation 1, the sampled EKG signal is fed into VF-Index Computation Unit 306 wherein it is shifted by half a period (i.e., T/2) and added to the original signal. The sum of the absolute values of the resultant residual signal is then computed and normalized within VF-Index Computation Unit 306 utilizing the following equation:

$$VF\text{-Index} = \frac{\Sigma |V(j) + V(j - T/2)|}{\Sigma [|V(j)| + |V(j - T/2)|]} \quad \text{(Eq. 2)}$$

Note that here, for sake of clarity, the VF filter leakage, as Equation 2 is described in the foregoing cited reference, is described here as the VF-Index. Thereafter, the computed VF-Index is fed to Threshold Comparison Unit 308, wherein the VF-Index is compared to a threshold value. Currently, VF is declared if the VF-Index is small (i.e., is less than a preselected threshold). (See Kuo and Dillman page 348).

In rough overview, what the foregoing method does is analogize the waveform to a sinusoidal with estimated period T approximated by Equation 1, "slip" the analogized waveform a half period, and sum the original and "slipped" waveform. Thus, for a waveform that has some degree of regularity (i.e., has some degree of regularity from cycle to cycle within the wave), the summation will have a minimum at a delay of about one-half the amount of time that is required for the waveform to completely repeat itself.

The VF/VT automated detection method as described works well when the waveforms presented resemble the sinusoidal (e.g. ventricular flutter). The symmetric characteristics of the waveform produce excellent cancellation after copies of the signal have been shifted and superimposed onto the original signal. However, when the signals become more chaotic, the cancellation after superimposition is poor (producing a large normalized residual) hence making it more difficult to detect ventricular fibrillation.

Over the past eighteen year period, significant effort has been made to increase the overall accuracy of the described VF/VT automated detection method. Currently utilized methods are to use various and different VF filter leakage threshold levels in order to attempt to detect various and different arrhythmias. However, such currently utilized methods which try to detect the more chaotic arrhythmias (e.g., using a higher threshold for detection) tend to be problematical (e.g., allowing a detector to be more sensitive, under presently utilized methods, also generally increases the likelihood of false positive detection; the converse also tends to be true).

Thus, it is apparent from the foregoing that a need exists for a method and apparatus which yield an automated analysis of waveform representations of heart function produced by an electrocardiographic device, and where such method and apparatus enhance both the sensitivity and selectivity of the automated detection of arrhythmias within even highly chaotic waveform representations of heart function.

SUMMARY OF THE INVENTION

It is therefore one object of the present invention to provide a method and apparatus which yield an automated analysis of waveform representations of heart function.

It is another object of the present invention to provide a method and apparatus which yield an automated analysis of waveform representations of heart function produced by an electrocardiographic device.

It is yet another object of the present invention to provide a method and apparatus which yield an automated analysis of waveform representations of heart function produced by an electrocardiographic device, and where such method and apparatus enhance both the sensitivity and selectivity of the automated detection of arrhythmias within even highly chaotic waveform representations of heart function.

The foregoing objects are achieved as is now described. The method and apparatus accomplish their objects via the following. An indicator of triangular-like components within a waveform representation of heart function is calculated. An indicator of an area encompassed by the waveform representation indicative of heart function is calculated. A ratio is calculated utilizing the calculated indicator of an area and calculated indicator of triangular-like components to assess the chaotic nature of the waveform representation of heart function. Additionally, a ventricular fibrillation index is calculated. The calculated ventricular fibrillation index is utilized, in two dimensional space, with the ratio that is calculated utilizing the calculated indicator of an area and the calculated indicator of triangular-like components to assess the likelihood of ventricular fibrillation based upon waveform representation of heart function. Further additionally, a minimum ventricular fibrillation index is calculated. The calculated minimum ventricular fibrillation index is utilized, in two dimensional space, with the ratio that is calculated utilizing the calculated indicator of an area and the calculated indicator of triangular-like components to assess the likelihood of ventricular fibrillation based upon waveform representation of heart function. The minimum calculated ventricular fibrillation is also utilized in one dimensional space to assess the likelihood of ventricular fibrillation based upon waveform representation of heart function.

The above as well as additional objects, features, and advantages of the present invention will become apparent in the following detailed written description.

DESCRIPTION OF THE DRAWINGS

The novel features believed characteristic of the invention are set forth in the appended claims. The invention itself, however, as well as a preferred mode of use, further objects, and advantages thereof, will best be understood by reference to the following detailed description of an illustrative embodiment when read in conjunction with the accompanying drawings, wherein:

DETAILED DESCRIPTION OF PREFERRED EMBODIMENT

One aspect of the method and apparatus, set forth later, which can analyze even highly chaotic waveform representation of heart function, and on the basis of such analysis both selectively and sensitively detect the presence of arrhythmia, involves the problem of optimizing detector performance. The problem of optimizing a detector's performance involves the selection of a threshold such that the probability of error (total number of false positives and false negatives) is minimized.

Figure 1A:
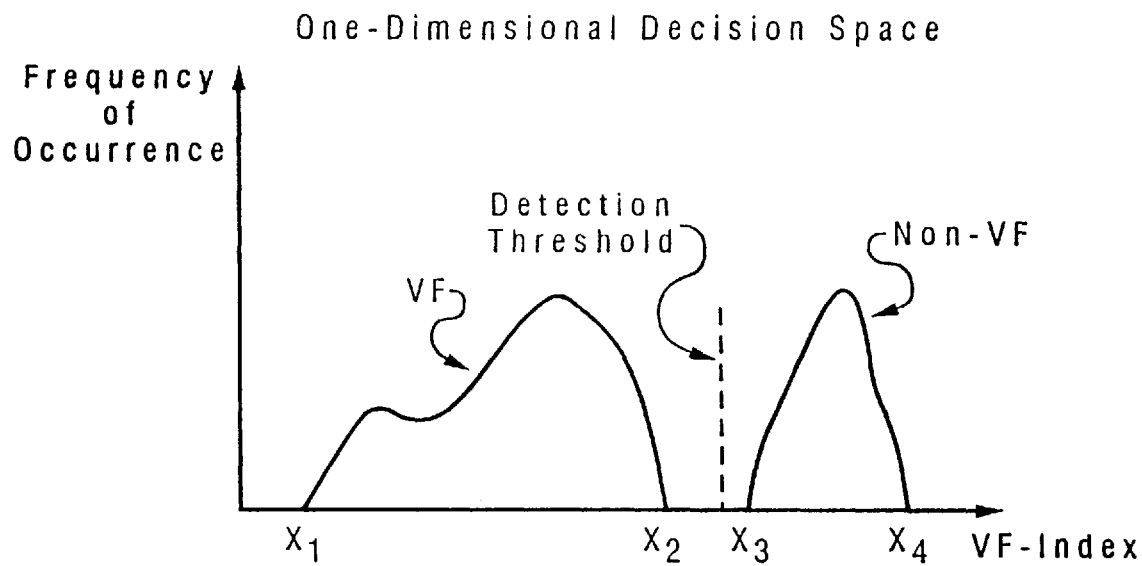
FIG. 1A illustrates issues involved in optimizing a detector.

Refer now to FIG. 1A, which illustrates issues involved in optimizing a detector. Shown in FIG. 1A is an exemplar graphical plotting of the frequency of occurrence of a VF-Index for non-VF waveforms and VF waveforms (the VF-Index is an indicator of the presence of Ventricular Fibrillation; the way in which the VF-Index is calculated in a preferred embodiment will be set forth later in the discussion). Since in FIG. 1A the plots of the frequency of occurrence of the VF-Index for the two types (non-VF and VF waveforms) do not overlap, any threshold value between X2 and X3 will work well (thereby minimizing false positives and false negatives). Thus, FIG. 1A depicts the ideal case wherein detection is relatively straightforward in that there is no overlap in X (VF-Index) values where both VF and non-VF are occurring.

Figure 1B:
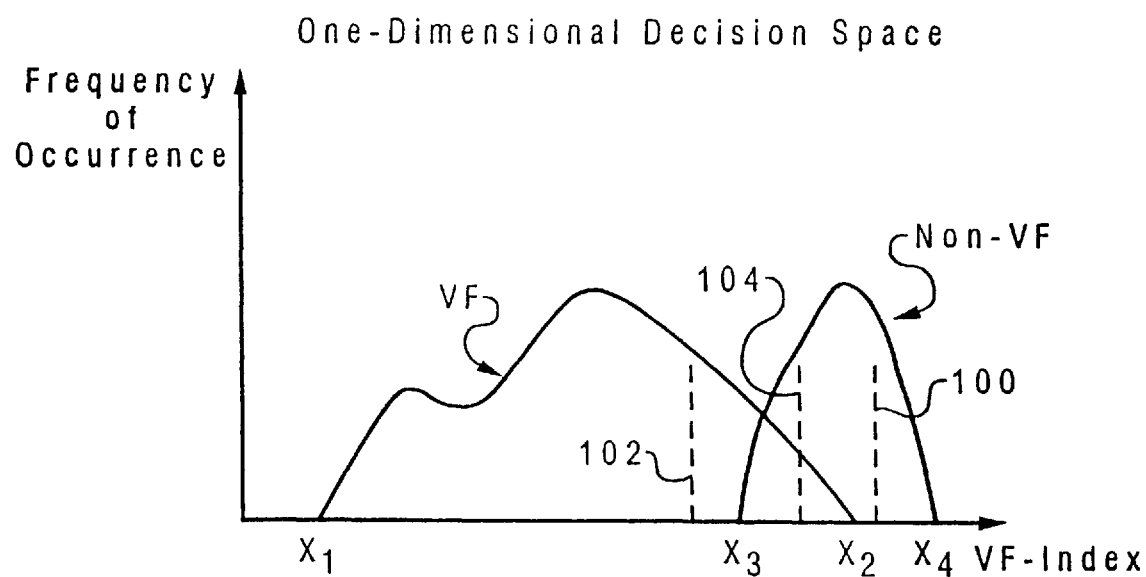
FIG. 1B illustrates issues involved in optimizing a detector when detection criteria overlap.

Unfortunately, like most real-life problems, the method described here for VF detection does not generate a non-overlapping VF-Index frequency of occurrence graphs in the decision space. FIG. 1B depicts the real-life problems associated with optimizing a VF detector. Shown in FIG. 1B is an exemplar graphical plotting of the frequency of occurrence of the VF-Index for non-VF waveforms and VF waveforms. Notice that, unlike the situation shown in FIG. 1A, there is definite overlap of the graphical plots. Specifically, at any point along the X axis between X3 and X2, one can draw a vertical line extending upward parallel to the frequency of occurrence axis, which will intersect both the frequency of occurrence graphs for both non-VF and VF waveforms. In practical terms, what this means is that three different threshold values are of interest: (1) a threshold value chosen to be between X2 and X4, such as detection threshold 100, wherein values below such a threshold will be judged to be VF, although as shown in FIG. 1B some of the such values could also be representative of non-VF EKGs, in which case a false positive can possibly occur; (2) a threshold value chosen to be between X1 and X3, such as detection threshold 102, wherein values above such threshold will be judged to be non-VF, although as shown in FIG. 1B some of such values could still be representative of VF, in which case a false negative can possibly occur; and (3) a threshold value chosen to be between X2 and X3, such as detection threshold 104, wherein both false positive and false negatives can possible occur. Tradeoffs between false positive and false negative must be made in selecting the threshold. While tradeoffs can be made by changing the threshold value, the overall performance (measured in terms of both false positive and false negative) cannot be improved.

It was shown in FIG. 1B that the real-life behavior of the VF-Index frequency of occurrence graphs overlap. Formally, it may be stated that the real-life behavior of the VF-Index frequency of occurrence graphs overlap in a one dimensional decision space (i.e., using only a single feature derived from the signal).

Figure 2:
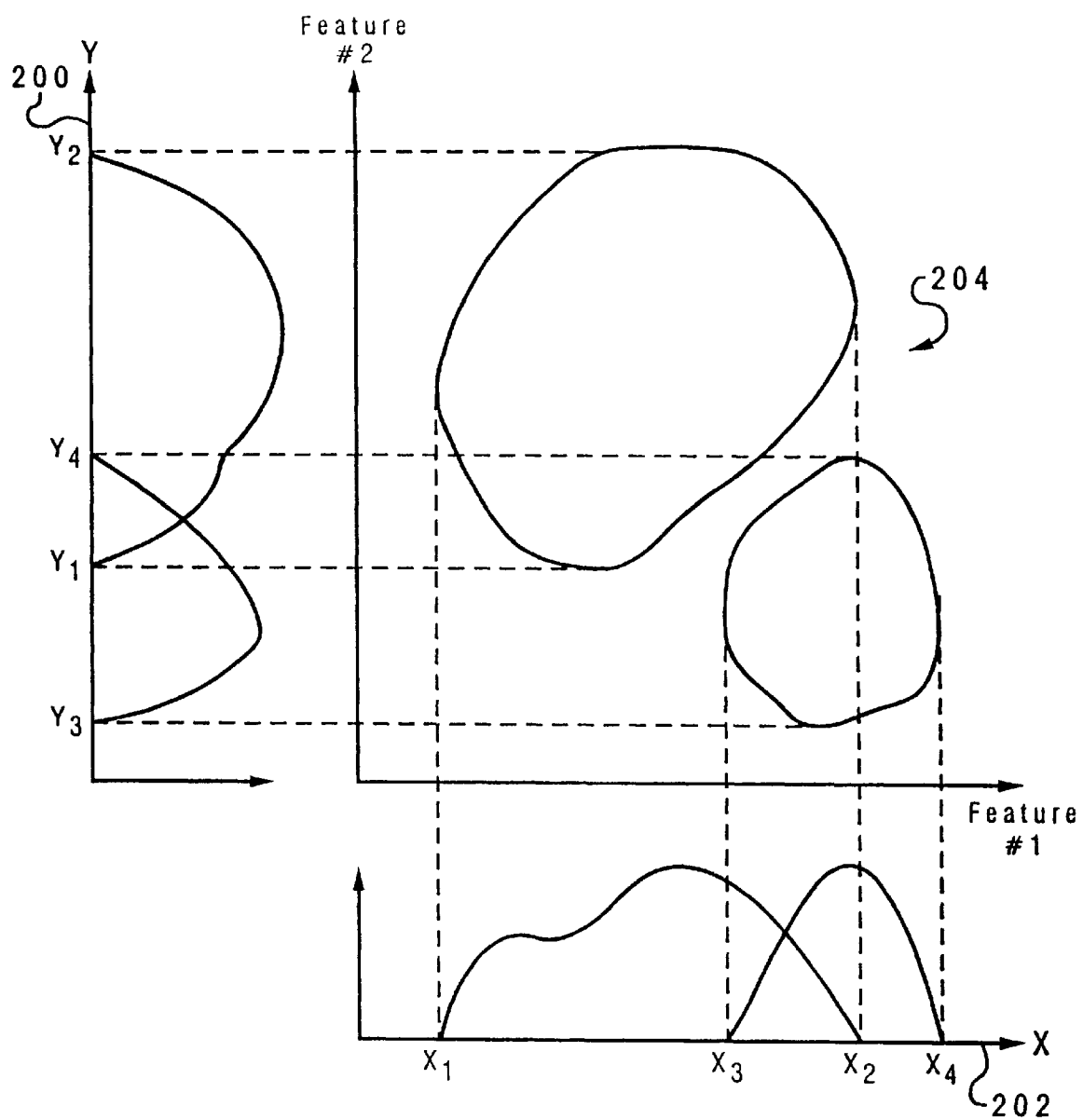
FIG. 2 illustrates issues involved in the use of two dimensional decision space to optimize a detector.
Figure 3:
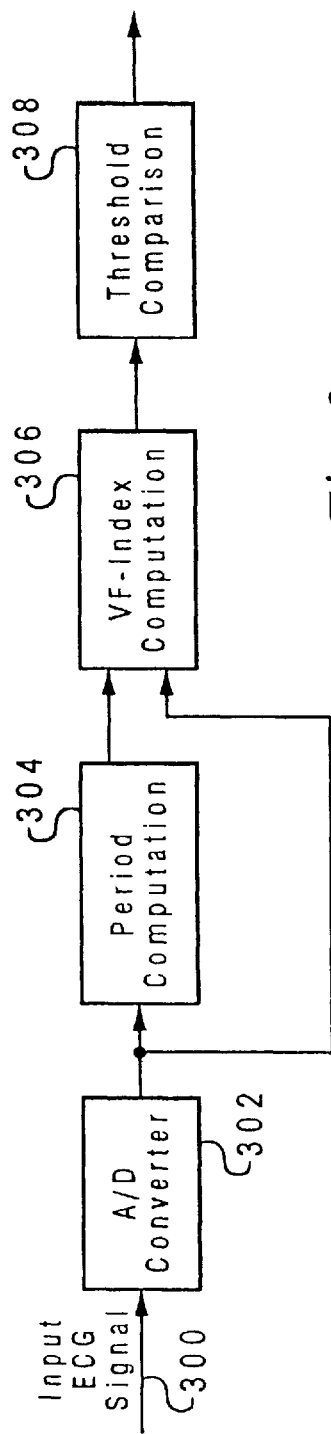
FIG. 3 shows a simplified block diagram of a background art VF detector as set forth in reference cited.

By looking at multiple features (i.e., a higher dimensional decision space) it is sometimes possible to produce non-overlapping distributions so that an unambiguous decision (no false positives and false negatives) can be made or distributions with smaller overlapping region so that a better decision (fewer false positives and false negatives) can be made. An example in a two dimensional decision space is illustrated in FIG. 2. Although the two individual graphical plots 200, 202 shown in FIG. 2 overlap in each of the one dimensional decision spaces (i.e., by looking at each feature independently), they do not overlap in the two dimensional decision space 204 (i.e., by looking at both features simultaneously). That is, a two dimensional threshold can be utilized to eliminate the overlapping problems present in both of the one dimensional graphical plots shown. Therefore, one way to improve the overall performance of the VF detection method is to see whether it is possible to find other features associated with the signal that will produce a more favorable distribution (i.e., either non-overlapping or a smaller overlapping region) when used together with the overlapping VF-Index (such as was shown overlapping in FIG. 1B) in a higher dimensional decision space.

In an illustrative embodiment of the present invention, there is described an additional feature that can be used together with the aforementioned VF-Index in a two dimensional decision space to further improve the overall performance of the VF detector. This new feature is the previous quantity which was introduced and referred to as the period estimate T in Equation 1. However, although the quantity will continue to be referred to as T throughout, as will be shown below, as utilized herein T will be additionally utilized as an indication of the degree of chaos in any particular signal; that is, as utilized herein, the numerator and denominator of T will be interpreted as somewhat indicative of the morphology of a signal, and hence it will be shown that the quotient of the numerator and denominator can be utilized as indicative of the degree of chaos in an EKG signal.

As utilized herein, general Equation 1 set forth above will have the following specific form:

$$T = 2\pi \frac{\sum\limits_{j=n-K}^{n} |V(j)|}{\sum\limits_{j=n-K}^{n} |V(j) - V(j-1)|} \qquad \text{(Eq. 3)}$$

where $V_{(j)}$ is the amplitude of the EKG's jth sample point; n is the current sample point; and K is the width, in samples, of the time window over which the summation is to be taken. The width of the time window over which the summation is to be taken, in time, will be as understood as that sufficient to detect VF by those skilled in the art (generally some interval of between 2 and 4 seconds in duration).

Utilizing Equation 3 with an incoming EKG signal $V_{(j)}$, a period estimate T can be computed. As utilized herein, the equation for VF-Index has the following specific form:

$$\text{VF-Index} = \frac{\sum_{j=n-L}^{n} |V(j) + V(j - T/2)|}{\sum_{j=n-L}^{n} [|V(j)| + |V(j - T/2)|]} \quad \text{(Eq. 4)}$$

where $V_{(j)}$ is the amplitude of the EKG's jth sample point; n is the current sample point; and L is the width, in samples, of the time window over which the summation is to be taken. The width of the time window over which the summation is to be taken, in time, will be as understood as that sufficient to detect VF by those skilled in the art (generally some interval of between 2 and 4 seconds in duration).

An alternate name for this VF-Index could be the normalized residual. The value of the normalized residual (or VF-Index) ranges from 0 to 1.

Figure 4:
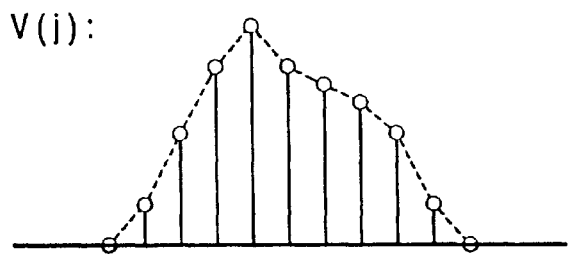
FIG. 4 depicts a graphical interpretation of the numerator of the formula as set forth in Equation 3.

FIG. 4 depicts a graphical representation of a waveform and the numerator of the formula as set forth in Equation 3. Shown in FIG. 4 is that the numerator can be likened to the area under the signal. That is, while the calculation of the area under the signal would require that each sample value be multiplied by the sample width, what is shown in FIG. 4 is just the sum of the sample values. Thus, that sum can be "likened to" what would have occurred had the time sample been used but subsequently removed from the equation by factoring it out of the summation. Such sum can also be "likened to" the area that would have been calculated had the time sample been used after being normalized.

Figure 5:
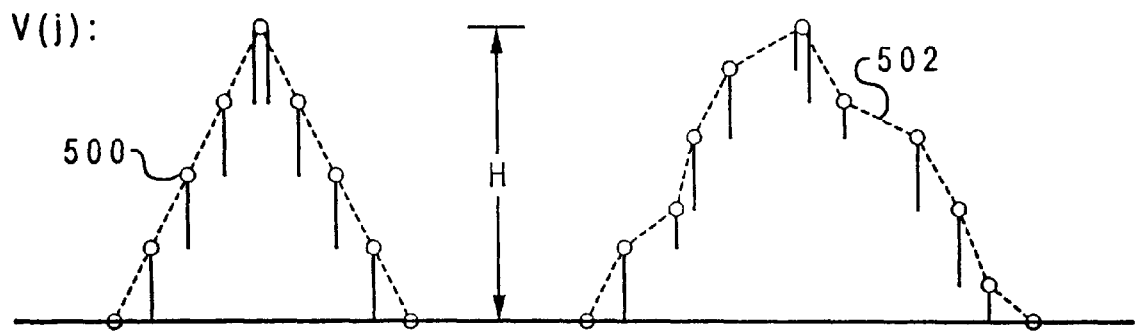
FIG. 5 illustrates graphical interpretations of the denominator of the formula as set forth in Equation 3.

FIG. 5 illustrates the fact that for a triangular waveform 500 the sum of the absolute values of the differences between two adjacent samples is equal to twice the height (2H) of the triangular signal. FIG. 5 also illustrates the fact that the sum of the absolute values of the differences between two adjacent samples is equal to twice the height ultimately reached by a signal regardless of the actual morphology of the signal, provided that the sampled values are monotonically non-decreasing before the ultimate maximum value is reached and the sample values are monotonically non-increasing subsequent to the ultimate maximum value and until the endpoint is reached, provided that the starting and ending points for the signal have the same magnitude. FIG. 5 illustrates this by reference to irregular shaped waveform 502. This fact will be utilized below to estimate the degree of chaos in a particular signal.

Taken together, FIGS. 4 and 5, and the discussions accompanying them, can be utilized to interpret the equation for T as used herein (Equation 3) as an indicator of the chaos, or irregularity, within any particular signal. FIG. 4 illustrated that the numerator can be interpreted as the area under some particular signal. FIG. 5 illustrated that the sum of the absolute values of difference between two adjacent samples is equal to the ultimate height reached by the signal, regardless of morphology. Thus, regardless of the actual morphology of any signal, such a signal can generally conceptually thought of as being broken up into triangular-like chunks (the term triangular-like is used to indicate that the sum of the absolute value of the differences of waveforms discussed in relation to FIG. 5 equate to twice the height ultimately reached; as has been discussed such excursions can be any morphology, so long as they start and end at virtually the same level). Hence, each triangular-like excursion of the signal will contribute to the denominator of Equation 3 by an amount somewhat approximately equal to twice the height of an excursion. Consequently, for two signals with the same area (and hence having the same numerator in Equation 3), the signal which is more chaotic (namely with more excursions or turning points) will have a larger denominator (there will be more triangular-like excursions and hence larger contributions to the denominator from the more numerous excursions). Consequently, the equation for T will yield a smaller T value for such signals. Thus, T can serve as a relative indicator of chaos in signals.

From the foregoing described observations, it is clear that a relationship exists between the estimated T and the degree of chaos of the signal (or the resultant normalized residual). For a more chaotic signal (such as VF signal) the signal will have a larger normalized residual (due to poor signal cancellation) and a smaller T value (due to a larger denominator value). On the other hand, for a more sinusoidal signal, the signal will have a smaller normalized residual (due to good signal cancellation) and a larger T value (due to a smaller denominator value).

Note that in addition to the reason explained above, there is another factor that may also cause the normalized residual (VF-Index) to increase. As has been shown earlier, the period estimate T is derived based on the assumption that the signal is sinusoidal. For a chaotic signal which does not resemble sinusoidal, the period estimate computed may not produce the best signal cancellation in the normalized residual computation. However, it has been found that this effect can be eliminated by shifting the signal left and right around the half period point until a minimum value is obtained in the VF-Index computation. This finding can be utilized to increase the accuracy of detection, as will be shown below in relation to FIG. 7 and FIG. 9. On the other hand, the increase of the normalized residual due to the chaos of the signal itself cannot be eliminated by shifting in the VF-Index computation.

What will now be disclosed is how the observation that there exists a relationship between the calculated period T and the degree of chaos of the EKG signal can be utilized in conjunction with the VF-Index disclosed to provide a method and apparatus for VF detection that are much more selective and sensitive to methods and systems extant previously. By expanding from a single dimensional decision space (i.e., one which uses the VF-Index only, much as was illustrated in FIG. 2) to a two dimensional decision space (i.e., one which uses both the VF-Index and the period estimate T) in VF detection, the overall performance (both false positive and false negative) can be improved.

Figure 6:
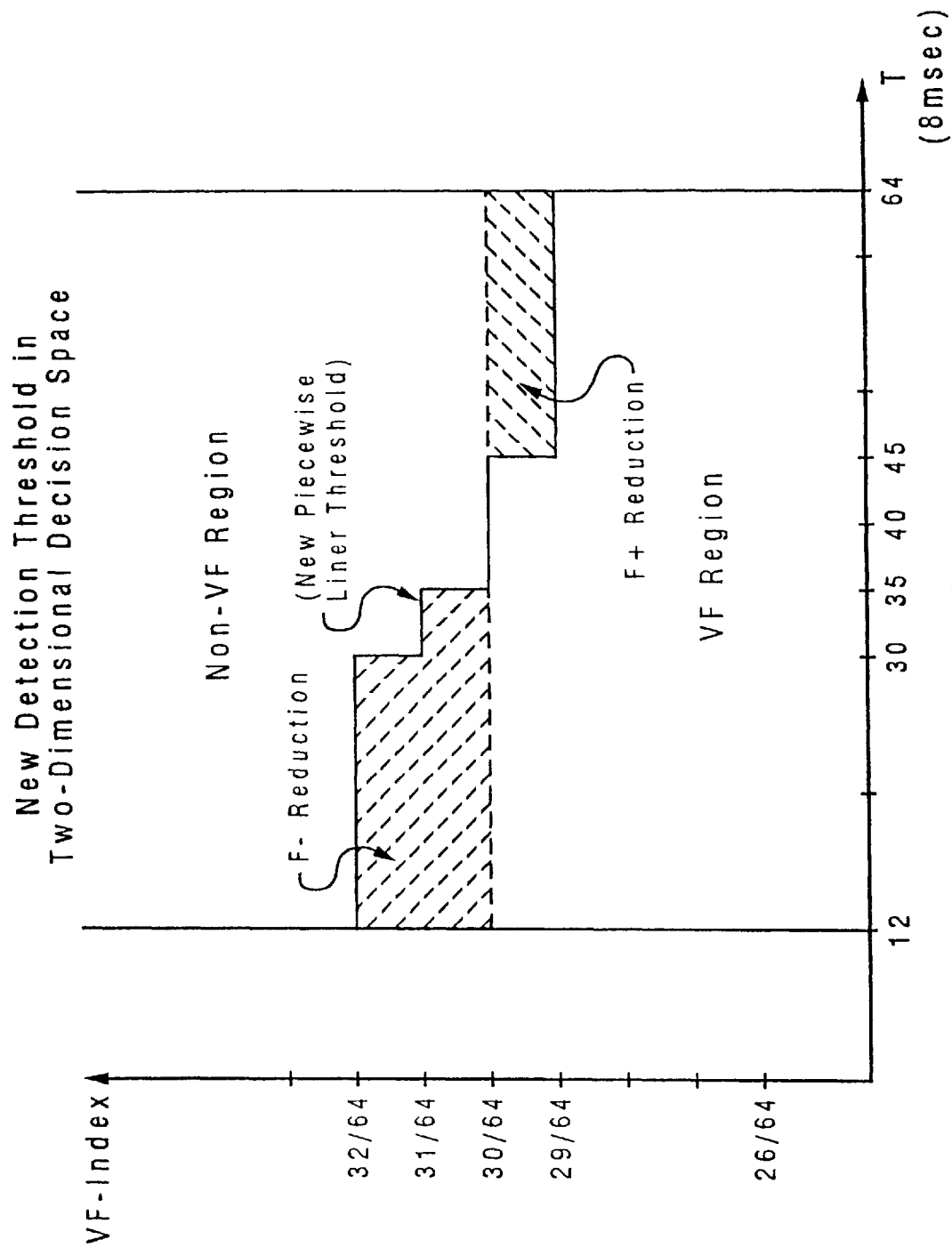
FIG. 6 depicts an illustration of an optimal detection threshold for an illustrative embodiment of the present invention.

FIG. 6 depicts an illustration of an optimal detection threshold for an illustrative embodiment of the present invention. Such an optimal decision threshold can be determined empirically by finding a decision line such that the probability of error is minimized in the two dimensional decision space spanned by the VF-Index and the period estimate T. This decision threshold is a function of both the VF-Index and the period T. In practice, it has been found that a simple piecewise linear threshold function works sufficiently well.

The simple piecewise linear threshold function is shown graphically in FIG. 6 and can be described as follows:

| Period Estimate T (8 msec sample) | VF-Index |
|---|---|
| <30 | <32/64 |
| >= 30 and <35 | <31/64 |
| >= 35 and <45 | <30/64 |
| >= 45 | <29/64 |

It has been discussed that a small T value is produced when the signal is VF (more chaotic). Therefore, a higher threshold value on the VF-Index is used to make it easier to detect VF. Using this higher value further increases the sensitivity of the detector (labeled as False Negative (F⁻) reduction in FIG. 6). On the other hand, a lower threshold value on the VF-Index is used when the T value is larger (less likely to be VF), hence making it more difficult to call the waveform VF. Using this lower threshold value will reduce false positive detection (labeled as False Positive (F⁺) reduction in FIG. 6). Therefore, not only has the foregoing illustrated method, wherein both features (VF-Index and calculated T) are utilized simultaneously, increased the sensitivity of the detector, but it has also reduced the potential of false positive detection. Furthermore, since the additional feature used, period estimate T, is necessarily computed in order to generate the VF-Index, the performance enhancement generated by the two dimensional decision space solution has virtually no additional processing costs associated with it.

Figure 7:
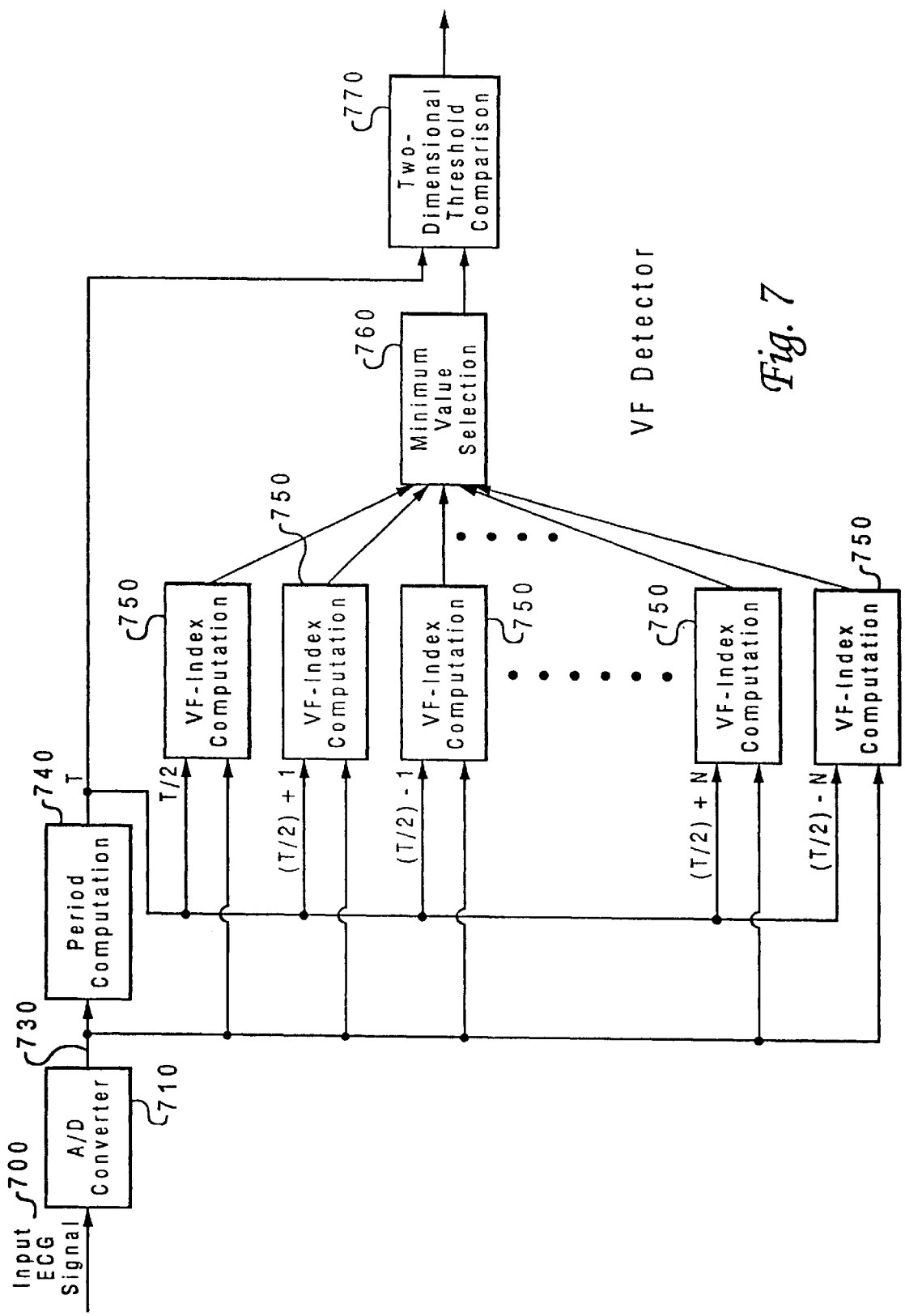
FIG. 7 illustrates a block diagram of an illustrative system embodiment.

FIG. 7 shows a block diagram of an illustrative system embodiment. In FIG. 7, the minimum VF-Index is computed by incrementally shifting the signal around the estimated half-period T/2. The maximum amount of correction N is a design parameter selected to optimize the overall VF detection performance. Shown in FIG. 7 is that an input EKG signal 700 is fed into an A/D Converter 710. Subsequently, digitized input EKG signal 730 is fed into Period Computation Device 740. Period Computation Device 740 utilizes Equation 3 to compute T.

After T has been computed, FIG. 7 illustrates that computed T, along with digitized input EKG signal 730, is then fed to multiple VF-Index Computation Units 750 which compute the VF-Index utilizing the VF-Index computation formula (Equation 4) set forth previously. As is shown in FIG. 7, multiple VF-Indices are calculated by shifting the signal incrementally around the estimated half-period T/2. Thereafter, the computed VF-Indices are fed into Minimum Value Selection Unit 760 which determines the minimum computed VF-Index and selects it. Thereafter, the minimum computed VF-Index, together with the computed estimate of T from Period Computation Device 740, are fed to Two-Dimensional Threshold Comparison Device 770 which performs the comparisons similar to those shown in FIG. 6 to determine whether or not the input EKG analyzed is consistent with VF or non-VF.

Figure 8:
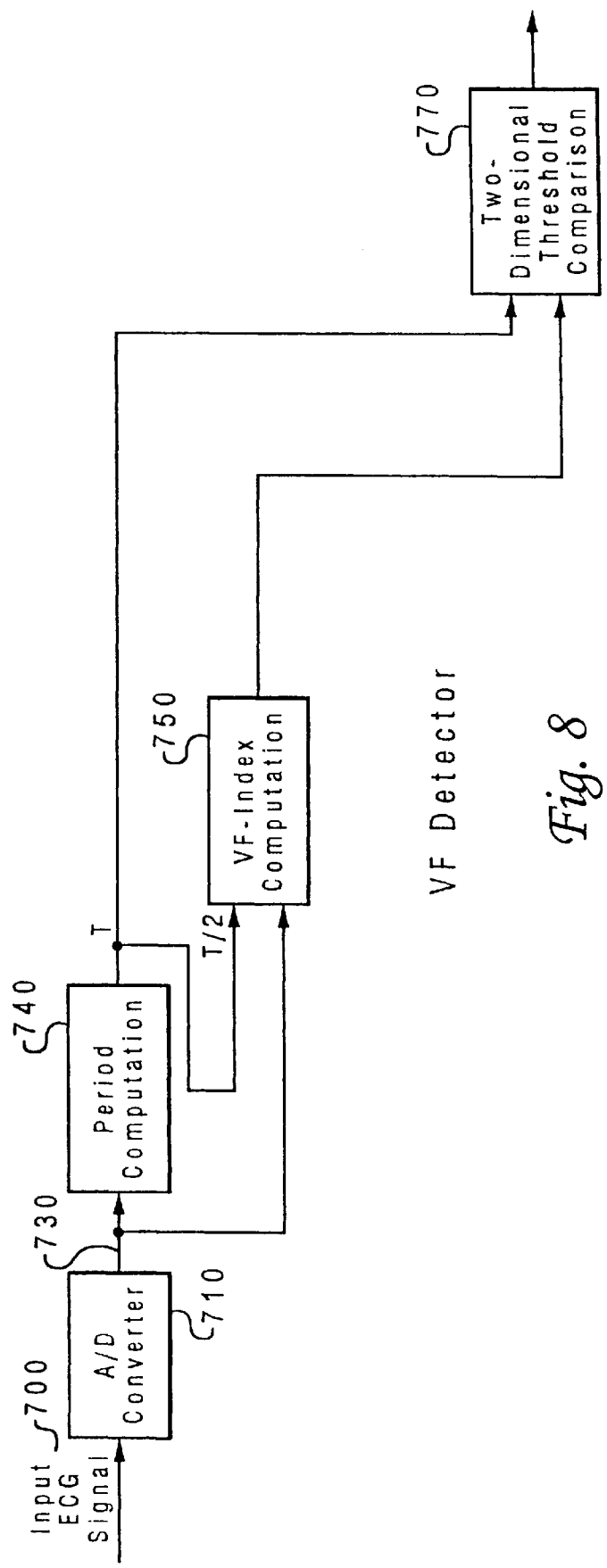
FIG. 8 depicts another embodiment wherein only one VF-Index Computation Unit is utilized.

FIG. 7, as just described, described an embodiment wherein a minimum VF-Index was computed and used in conjunction with a two-dimensional threshold. FIG. 8 sets forth another embodiment wherein minimum VF-Index is not computed. Rather, in this embodiment, only one VF-Index Computation Unit 750 is utilized to calculate a single VF-Index.

Shown in FIG. 8 is that an input EKG signal 700 is fed into an A/D Converter 710. Subsequently, digitized input EKG signal 730 is fed into Period Computation Device 740. Period Computation Device 740 utilizes Equation 3 to compute T.

After T has been computed, FIG. 8 illustrates that computed T, along with digitized input EKG signal 730, is then fed to a single VF-Index Computation Unit 750 which computes the VF-Index utilizing the VF-Index computation formula (Equation 4) set forth previously. This VF-Index is fed, along with estimated T from Period Computation Unit 740, into Two-Dimensional Threshold Comparison Device 770 which performs the threshold comparisons associated with FIG. 6 to determine whether or not the input EKG analyzed is consistent with VF or non-VF.

Figure 9:
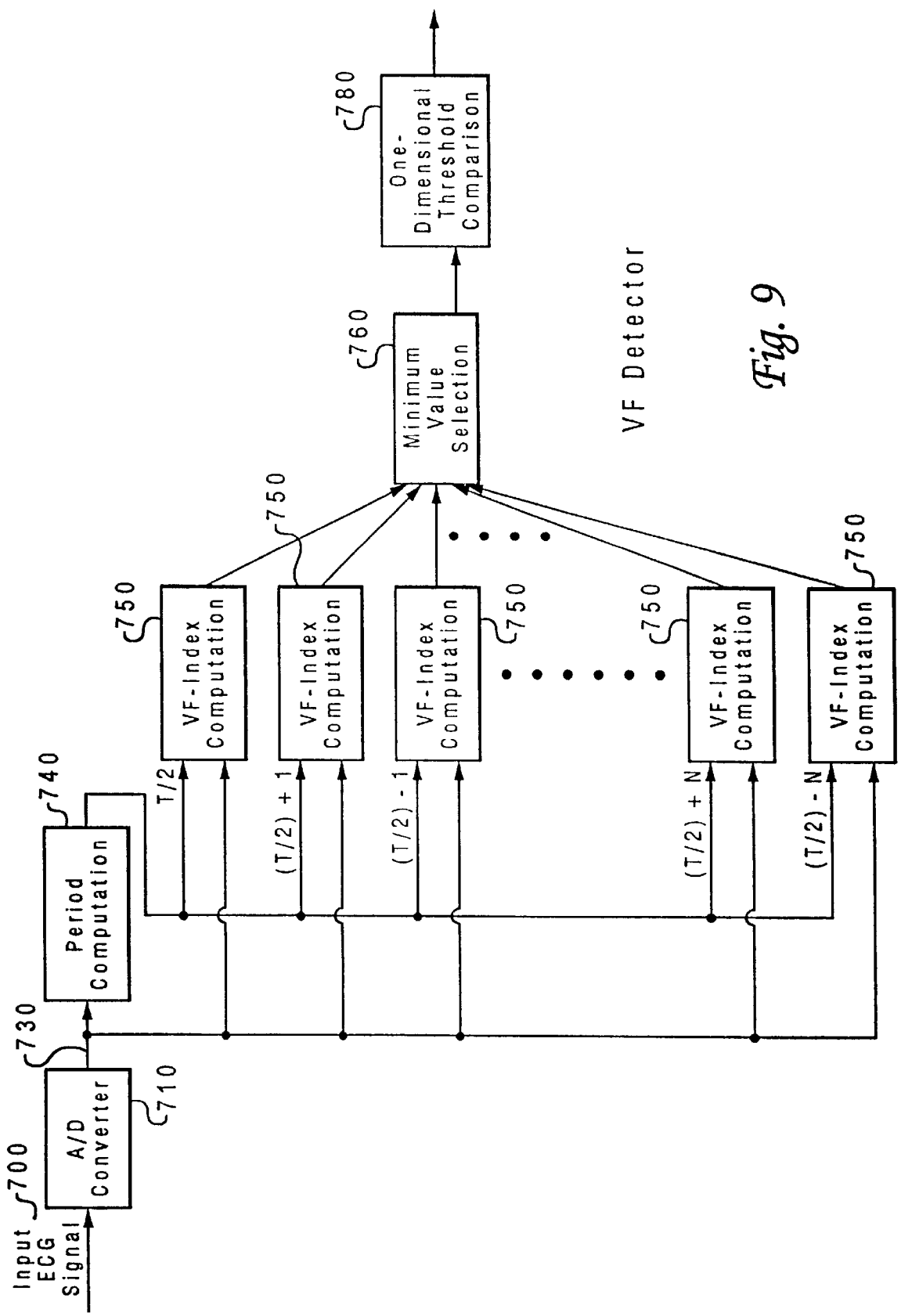
FIG. 9 depicts a third embodiment wherein the above referenced finding that a more accurate VF-Index can be obtained by incrementally shifting waveforms relative to estimated T/2 is utilized with a one-dimensional threshold to improve accuracy in VF detection.

Refer now to FIG. 9. FIG. 9 sets forth a third embodiment wherein the above referenced finding that a more accurate VF-Index can be obtained by incrementally shifting waveforms relative to estimated T/2 is utilized with a one-dimensional threshold to improve accuracy in VF detection. Shown in FIG. 9 is that an input EKG signal 700 is fed into an AND Converter 710. Subsequently, digitized input EKG signal 730 is fed into Period Computation Device 740. Period Computation Device 740 utilizes Equation 3 to compute T.

After T has been computed, FIG. 9 illustrates that computed T, along with digitized input EKG signal 730, is then fed to multiple VF-Index Computation Units 750 which compute the VF-Index utilizing the VF-Index computation formula (Equation 4) set forth previously. As is shown in FIG. 9, multiple VF-Indices are calculated by shifting the signal incrementally around the estimated half-period T/2. Thereafter, the computed VF-Indices are fed into Minimum Value Selection Unit 760 which determines the minimum computed VF-Index and selects it. Thereafter, the minimum computed VF-Index is fed to One-Dimensional Threshold Comparison Device 780 to determine whether or not the input EKG analyzed is consistent with VF or non-VF.

The foregoing has introduced an empirically derived piecewise linear threshold function optimized for use without shifting of the waveform to be analyzed (i.e., as in the embodiment illustrated in FIG. 8). Those skilled in the art will recognize that other optimized threshold functions can also be empirically obtained utilizing the above disclosed information. Those skilled in the art will also recognize that such threshold functions will be dependent upon the specific values of parameters chosen (for example, the parameters K (width of time window in samples for Equation 3), L (width of time window in samples for Equation 4), and N (the ultimate magnitude of time by which waveforms are shifted relative to an estimated T/2). That is, those skilled in the art will realize that a change in one or more parameters will generally give rise to the need to empirically redetermine optimum threshold values.

Figure 10:
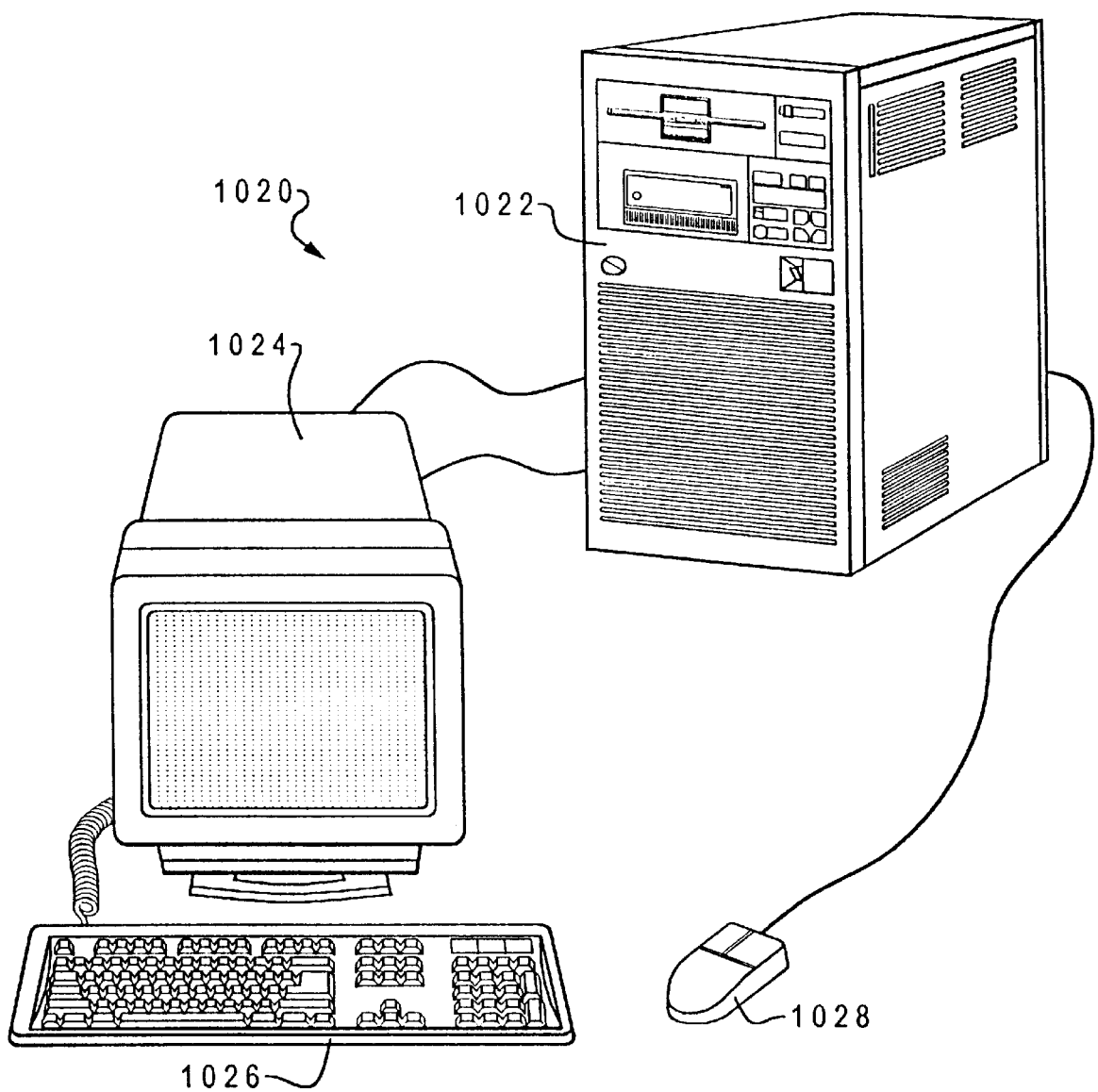
FIG. 10 depicts a pictorial representation of a data-processing system which can be utilized in accordance with the method and apparatus of an illustrative embodiment of the present invention.

With reference now to the figures and in particular with reference now to FIG. 10, there is depicted a pictorial representation of a data-processing system which can be utilized in accordance with the method and apparatus of an illustrative embodiment of the present invention. The method and apparatus provided by an illustrative embodiment of the present invention can be implemented with the data-processing system depicted in FIG. 10. A computer 1020 is depicted which includes a system unit 1022, a video display terminal 1024, a keyboard 1026, and a mouse 1028. Computer 1020 may be implemented utilizing any suitably powerful computer, such as commercially available mainframe computers, minicomputers, or microcomputers.

Figure 11:
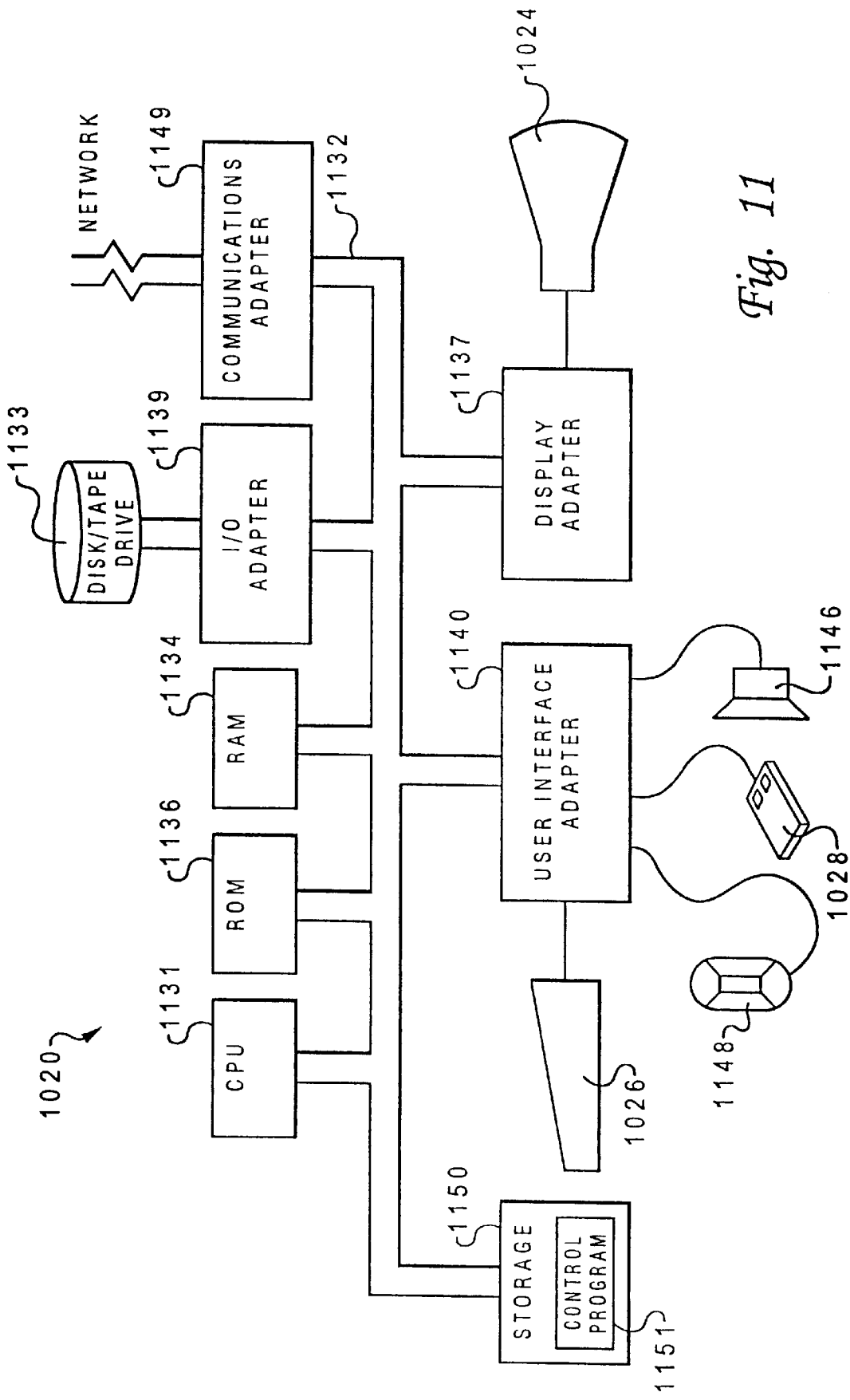
FIG. 11 is an illustration of a representative hardware environment which can be utilized in accordance with the method and apparatus of an illustrative embodiment of the present invention.

FIG. 11 is an illustration of a representative hardware environment which can be utilized in accordance with the method and apparatus of an illustrative embodiment of the present invention. FIG. 11 depicts selected components in computer 1020 in which an illustrative embodiment of the present invention may be implemented. System unit 1022 includes a Central Processing Unit ("CPU") 1131, such as a conventional microprocessor, and a number of other units interconnected via system bus 1132. Computer 1020 includes random-access memory ("RAM") 1134, read-only memory ("ROM") 1136, display adapter 1137 for connecting system bus 1132 to video display terminal 1024, and I/O adapter 1139 for connecting peripheral devices (e.g., disk and tape drives 1133) to system bus 1132. Video display terminal 1024 is the visual output of computer 1020, which can be a CRT-based video display well-known in the art of computer hardware. However, with a portable or notebook-based computer, video display terminal 1024 can be replaced with an LCD-based or a gas plasma-based flat-panel display. Computer 1020 further includes user interface adapter 1140 for connecting keyboard 1026, mouse 1028, speaker 1146, microphone 1148, and/or other user interface devices, such as a touch screen device (not shown), to system bus 1132. Communications adapter 1149 connects computer 1020 to a data-processing network.

Any suitable machine-readable media may retain the method and apparatus of an illustrative embodiment of the present invention, such as RAM 1134, ROM 1136, a magnetic diskette, magnetic tape, or optical disk (the last three being located in disk and tape drives 1133). Any suitable operating system and associated graphical user interface may direct CPU 1131. Other technologies can also be utilized in conjunction with CPU 1131, such as touch-screen technology or human voice control. In addition, computer 1020 includes a control program 1151 which resides within computer storage 1150. Control program 1151 contains instructions that when executed on CPU 1131 carries out the operations depicted and described in FIGS. 1, 2, 4, 5, 6, 7, 8, and 9 as necessary to implement the illustrative embodiments described herein.

Those skilled in the art will appreciate that the hardware depicted in FIG. 11 may vary for specific applications. For example, other peripheral devices such as optical disk media, audio adapters, or chip programming devices, such as PAL or EPROM programming devices well-known in the art of computer hardware, and the like may be utilized in addition to or in place of the hardware already depicted.

As a final matter, it is important that while an illustrative embodiment of the present invention has been, and will continue to be, described in the context of a fully functional computing system, those skilled in the art will appreciate that the mechanisms of an illustrative embodiment of the present invention are capable of being distributed as a program product in a variety of forms, and that an illustrative embodiment of the present invention applies equally regardless of the particular type of signal bearing media used to actually carry out the distribution. Examples of signal bearing media include recordable type media such as floppy disks, hard disk drives, CD ROMs, and transmission type media such as digital and analogue communication links.

While an illustrative embodiment has been particularly shown and described, it will be understood by those skilled in the art that various changes in form and detail may be made therein without departing from the spirit and scope of the illustrative embodiment.

What is claimed is:

1. A method for assessing the chaotic nature of a waveform representation of heart function, said method comprising the steps of:

calculating an indicator of triangular-like components within said waveform representation;

calculating an indicator of an area encompassed by said waveform representation;

calculating a ratio of said calculated indicator of an area and said calculated indicator of triangular-like components; and assessing the chaotic nature of said waveform representation of heart function by utilizing said ratio of said calculated indicator of an area and said calculated indicator of triangular-like components.

2. The method of claim 1, wherein said step of calculating an indicator of triangular-like components further comprises the steps of:

sampling said waveform representation of heart function to obtain successively sampled values; and summing the absolute values of the differences of said successively sampled values of said waveform representation of heart function.

3. The method of claim 1, wherein said step of calculating an indicator of an area further comprises the steps of:

sampling said waveform representation of heart function to obtain successively sampled values; and summing the absolute values of said successively sample values of said waveform representation of heart function.

4. The method of claim 1, wherein said step of assessing the chaotic nature of said waveform representation of heart function by utilizing said ratio further comprises the steps of:

generating a plurality of time-shifted versions of said waveform representation of heart function; and utilizing said ratio with said time-shifted versions of said waveforms to obtain a normalized residual such that said obtained normalized residual is indicative of the chaotic nature of said waveform.

5. A method for assessing the likelihood of ventricular fibrillation on the basis of a waveform representation of heart function, said method comprising the steps of:

calculating an indicator of triangular-like components within a waveform representation;

calculating an indicator of an area encompassed by said waveform representation;

calculating a ratio of said calculated indicator of an area and said calculated indicator of triangular-like components;

calculating a ventricular fibrillation index; and assessing the chaotic nature of said waveform representation of heart function by utilizing in at least a two-dimensional decision space said calculated ventricular fibrillation index with said ratio of said calculated indicator of an area and said calculated indicator of triangular-like components.

6. The method of claim 5, wherein said step of calculating a ventricular fibrillation index further comprises the steps of:

sampling said waveform representation of heart function to obtain successively sampled values;

summing the absolute values of at least one sum drawn upon a sampled value of said waveform and a previously sampled value of said waveform;

summing the values of at least one sum drawn upon the absolute value of said sampled value and the absolute value of said previously sampled value of said waveform; and calculating said ventricular fibrillation index based upon said summed absolute values of said at least one sum and said summed values of at least one sum drawn upon the absolute value of said sampled value and the absolute value of said previously sampled value.

7. The method of claim 5, wherein said step of calculating a ventricular fibrillation index further comprises the steps of:

generating a plurality of time-shifted versions of said waveform representation of heart function;

calculating a plurality of ventricular fibrillation indices based upon said plurality of time-shifted versions of said waveform representation of heart function; and selecting said calculated ventricular fibrillation index to be the minimum ventricular fibrillation index extant within said calculated plurality of ventricular fibrillation indices.

8. The method of claim 7, wherein said step of calculating a plurality of ventricular fibrillation indices further comprises the steps of:

calculating each of said plurality of ventricular fibrillation indices by doing the following for each of said plurality of time-shifted versions:

sampling each of said plurality of time-shifted versions to obtain successively sampled values;

summing the absolute values of at least one sum drawn upon a sampled value of each of said plurality of time-shifted versions and a previously sampled value of each of said plurality of time-shifted versions;

summing the values of at least one sum drawn upon the absolute value of said sampled value of each of said plurality of time-shifted versions and the absolute value of said previously sampled value of each of said plurality of time-shifted versions; and calculating said ventricular fibrillation index based upon said summed absolute values of said at least one sum and said summed values of at least one sum drawn upon the absolute value of said sampled value of each of said plurality of time-shifted versions and the absolute value of said previously sampled value of each of said plurality of time-shifted versions.

9. The method of claim 5, wherein said step of calculating an indicator of triangular-like components further comprises the steps of:

sampling said waveform representation of heart function to obtain successively sampled values; and summing the absolute values of the differences of successively sampled values of said waveform representation of heart function.

10. The method of claim 5, wherein said step of calculating an indicator of an area further comprises the steps of:

sampling said waveform representation of heart function to obtain successively sampled values; and summing the absolute values of successive sample values of said waveform representation of heart function.

11. The method of claim 5, wherein said step of utilizing, in at least a two-dimensional decision space, said calculated ventricular fibrillation index with a ratio of said calculated indicator of an area and said calculated indicator of triangular-like components further comprises the step of utilizing said calculated ventricular fibrillation index with a ratio of said calculated indicator of an area and said calculated indicator of triangular-like components in comparison with a two-dimensional comparison threshold to assess the likelihood of ventricular fibrillation.

12. A method for assessing the likelihood of ventricular fibrillation on the basis of a waveform representation of heart function, said method comprising the steps of:

calculating a minimum ventricular fibrillation index; and assessing the likelihood of ventricular fibrillation based upon a waveform representation of heart function by utilizing in at least a one-dimensional decision space said calculated minimum ventricular fibrillation index.

13. The method of claim 12, wherein said step of calculating a minimum ventricular fibrillation index further comprises the steps of:

calculating an estimated period for said waveform representation of heart function;

generating a plurality of time-shifted versions of said waveform representation of heart function shifted relative to said calculated estimated period;

calculating a plurality of ventricular fibrillation indices based upon said plurality of versions of said waveform representation of heart function shifted relative to said calculated estimated period; and selecting said calculated minimum ventricular fibrillation index to be the minimum ventricular fibrillation index extant within said calculated plurality of ventricular fibrillation indices.

14. The method of claim 13, wherein said step of calculating a plurality of ventricular fibrillation indices further comprises the steps of:

calculating each of said plurality of ventricular fibrillation indices by doing the following for each of said plurality of time-shifted versions:

sampling each of said plurality of time-shifted versions to obtain successively sampled values;

summing the absolute values of at least one sum drawn upon a sampled value of each of said plurality of time-shifted versions and a previously sampled value of each of said plurality of time-shifted versions;

summing the values of at least one sum drawn upon the absolute value of said sampled value of each of said plurality of time-shifted versions and the absolute value of said previously sampled value of each of said plurality of time-shifted versions; and calculating said ventricular fibrillation index based upon said summed absolute values of said at least one sum and said summed values of at least one sum drawn upon the absolute value of said sampled value of each of said plurality of time-shifted versions and the absolute value of said previously sampled value of each of said plurality of time-shifted versions.

15. The method of claim 13, wherein said step of calculating an estimated period further comprises the steps of:

sampling said waveform representation of heart function to obtain successively sampled values;

summing the absolute values of successive samples of said waveform;

summing the absolute value of the differences between successive samples of said waveform; and calculating said estimated period to be a ratio of said summed absolute values of successive samples to said summed absolute value of the differences between successive samples of said waveform.

16. An apparatus for assessing the chaotic nature of a waveform representation of heart function, said apparatus comprising:

means for calculating an indicator of triangular-like components within said waveform representation;

means for calculating an indicator of an area encompassed by said waveform representation;

means for calculating a ratio of said calculated indicator of an area and said calculated indicator of triangular-like components; and means for assessing the chaotic nature of said waveform representation of heart function by utilizing said ratio of said calculated indicator of an area and said calculated indicator of triangular-like components.

17. The apparatus of claim 16, wherein said means for calculating an indicator of triangular-like components further comprises:
   means for sampling said waveform representation of heart function to obtain successively sampled values;
   means for summing absolute values of the differences of successively sampled values of said waveform representation of heart function.

18. The apparatus of claim 16, wherein said means for calculating an indicator of an area further comprises:
   means for sampling said waveform representation of heart function to obtain successively sampled values; and
   means for summing absolute values of successive sample values of said waveform representation of heart function.

19. The apparatus of claim 16, wherein said means for utilizing said ratio further comprises:
   means for generating a plurality of time-shifted versions of said waveform representation of heart function; and
   means for utilizing said ratio with said time-shifted versions of said waveforms to obtain a normalized residual such that said obtained normalized residual is indicative of the chaotic nature of said waveform.

20. An apparatus for assessing the likelihood of ventricular fibrillation on the basis of a waveform representation of heart function, said apparatus comprising:
   means for calculating an indicator of triangular-like components within a waveform representation;
   means for calculating an indicator of an area encompassed by said waveform representation;
   means for calculating a ratio of said calculated indicator of an area and said calculated indicator of triangular-like components;
   means for calculating a ventricular fibrillation index; and
   means for assessing the likelihood of ventricular fibrillation based upon said waveform representation of heart function by utilizing in at least a two-dimensional decision space said calculated ventricular fibrillation index with a ratio of said calculated indicator of an area and said calculated indicator of triangular-like components.

21. The apparatus of claim 20, wherein said means for calculating a ventricular fibrillation index further comprises:
   means for sampling said waveform representation of heart function to obtain successively sampled values;
   means for summing absolute values of at least one sum drawn upon a sampled value of said waveform and a previously sampled value of said waveform;
   means for summing values of at least one sum drawn upon the absolute value of said sampled value and the absolute value of said previously sampled value of said waveform; and
   means for calculating said ventricular fibrillation index based upon said summed absolute values of said at least one sum and said summed values of at least one sum drawn upon the absolute value of said sampled value and the absolute value of said previously sampled value.

22. The apparatus of claim 20, wherein said means for calculating a ventricular fibrillation index further comprises:
   means for generating a plurality of time-shifted versions of said waveform representation of heart function;
   means for calculating a plurality of ventricular fibrillation indices based upon said plurality of time-shifted versions of said waveform representation of heart function; and
   means for selecting said calculated ventricular fibrillation index to be the minimum ventricular fibrillation index extant within said calculated plurality of ventricular fibrillation indices.

23. The apparatus of claim 22, wherein said means for calculating a plurality of ventricular fibrillation indices further comprises:
   means for calculating each of said plurality of ventricular fibrillation indices wherein said means for calculating is capable of doing the following functions for each of said plurality of time-shifted versions:
      sampling each of said plurality of time-shifted versions to obtain successively sampled values;
      summing absolute values of at least one sum drawn upon a sampled value of each of said plurality of time-shifted versions and a previously sampled value of each of said plurality of time-shifted versions;
      summing values of at least one sum drawn upon the absolute value of said sampled value of each of said plurality of time-shifted versions and the absolute value of said previously sampled value of each of said plurality of time-shifted versions; and
      calculating said ventricular fibrillation index based upon said summed absolute values of said at least one sum and said summed values of at least one sum drawn upon the absolute value of said sampled value of each of said plurality of time-shifted versions and the absolute value of said previously sampled value of each of said plurality of time-shifted versions.

24. The apparatus of claim 20, wherein said means for calculating an indicator of triangular-like components further comprises:
   means for sampling said waveform representation of heart function to obtain successively sampled values; and
   means for summing the absolute values of the differences of successively sampled values of said waveform representation of heart function.

25. The apparatus of claim 20, wherein said means for calculating an indicator of an area further comprises:
   means for sampling said waveform representation of heart function to obtain successively sampled values; and
   means for summing the absolute values of successive sample values of said waveform representation of heart function.

26. The apparatus of claim 20, wherein said means for utilizing, in at least a two-dimensional decision space, said calculated ventricular fibrillation index with a ratio of said calculated indicator of an area and said calculated indicator of triangular-like components further comprises means for utilizing said calculated ventricular fibrillation index with a ratio of said calculated indicator of an area and said calculated indicator of triangular-like components in comparison with a two-dimensional comparison threshold to assess the likelihood of ventricular fibrillation.

27. An apparatus for assessing the likelihood of ventricular fibrillation on the basis of a waveform representation of heart function, said apparatus comprising:
   means for calculating a minimum ventricular fibrillation index; and
   means for assessing the likelihood of ventricular fibrillation based upon a waveform representation of heart function by utilizing in at least a one-dimensional decision space said calculated minimum ventricular fibrillation index.

28. The apparatus of claim 27, wherein said means for calculating a minimum ventricular fibrillation index further comprises:

means for calculating an estimated period for said waveform representation of heart function;

means for generating a plurality of time-shifted versions of said waveform representation of heart function shifted relative to said calculated estimated period;

means for calculating a plurality of ventricular fibrillation indices based upon said plurality of versions of said waveform representation of heart function shifted relative to said calculated estimated period; and means for selecting said calculated minimum ventricular fibrillation index to be the minimum ventricular fibrillation index extant within said calculated plurality of ventricular fibrillation indices.

29. The apparatus of claim 28, wherein said means for calculating a plurality of ventricular fibrillation indices further comprises:

means for calculating each of said plurality of ventricular fibrillation indices wherein said means for calculating is capable of doing the following functions for each of said plurality of time-shifted versions:

sampling each of said plurality of time-shifted versions to obtain successively sampled values;

summing absolute values of at least one sum drawn upon a sampled value of each of said plurality of time-shifted versions and a previously sampled value of each of said plurality of time-shifted versions;

summing values of at least one sum drawn upon the absolute value of said sampled value of each of said plurality of time-shifted versions and the absolute value of said previously sampled value of each of said plurality of time-shifted versions; and calculating said ventricular fibrillation index based upon said summed absolute values of said at least one sum and said summed values of at least one sum drawn upon the absolute value of said sampled value of each of said plurality of time-shifted versions and the absolute value of said previously sampled value of each of said plurality of time-shifted versions.

30. The apparatus of claim 28, wherein said means for calculating an estimated period further comprises:

means for sampling said waveform representation of heart function to obtain successively sampled values;

means for summing absolute values of successive samples of said waveform;

means for summing an absolute value of the differences between successive samples of said waveform; and means for calculating said estimated period to be a ratio of said summed absolute values of successive samples to said summed absolute value of the differences between successive samples of said waveform.

* * * * *